United States Patent [19]

Huber

[11] Patent Number: 5,585,495
[45] Date of Patent: Dec. 17, 1996

[54] REDUCTION METHOD FOR SUBSTITUTED 5-METHYLENE-THIAZOLIDINEDIONES

[75] Inventor: Joel E. Huber, Mattawan, Mich.

[73] Assignee: The Upjohn Company, Del.

[21] Appl. No.: 397,130

[22] PCT Filed: Dec. 4, 1992

[86] PCT No.: PCT/US92/10329

§ 371 Date: Jun. 17, 1994

§ 102(e) Date: Jun. 17, 1994

[87] PCT Pub. No.: WO93/13095

PCT Pub. Date: Jul. 8, 1993

Related U.S. Application Data

[63] Continuation of Ser. No. 811,103, Dec. 20, 1991, abandoned.

[51] Int. Cl.$^6$ ............................................. C07D 277/34
[52] U.S. Cl. ................................................. 548/183
[58] Field of Search ...................................... 548/183

[56] References Cited

FOREIGN PATENT DOCUMENTS 139182  6/1988  Japan .

OTHER PUBLICATIONS

Y. Momose, K. Meguro, et. al., "Studies on Antidiabetic Agents X. Synthesis and Biological Activities of Pioglitazone and Realted Compounds" Chem. Pharm. Bull., 39:1440–1445 (1991).
Chemical Abstract, 109:6504h (1988).
D. A. Clark, et. al., "Substituted Dihydrobenzopyran Thiazolidine–2,4–diones as Hypoglycemic Agents", J. Med. Chem. 1991, 34, 319–325.
Drugs Fat., 1991 16(9) CS–045, EN: 105806.
Urs Leutenegger, et. al., "Enatioselective Reduction of α,β–Unsaturated Carboxylates with $NaBH_4$ and Catalytic Amounts of Chiral Cobalt Semicorrin Complexes" Angew. Chem. Int. Ed. Engl. 28 (1989) No. 1.
M. N. Ricroch, et. al., "Etude Du Mecanisme De L'Hydrogenation Des Esters Insatures Catalysee Par La Vitamine $B_{12}$ Ou Les Cobaloximes" J. Organometallic Chemistry, 67 (1974)119–129.

Primary Examiner—Robert Gerstl
Attorney, Agent, or Firm—Martha A. Gammill

[57] ABSTRACT

The present invention provides a method for making known pharmaceutical compounds. More particularly the present invention provides a new reduction method for making thiazolidinedione derivatives, particularly ciglitazone, pioglitazone, and englitazone. This reduction method comprises reacting a compound of the formula II with a cobalt ion, a ligand and a reducing agent to achieve a compound of the formula I.

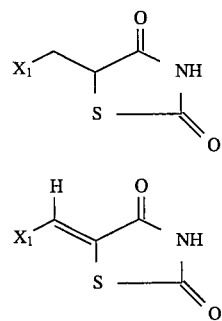

8 Claims, No Drawings

REDUCTION METHOD FOR SUBSTITUTED 5-METHYLENE-THIAZOLIDINEDIONES

FIELD OF INVENTION

This application is the national phase of international application PCT/US92/10329, filed 4 Dec. 1992, which is a continuation-in-part of U.S. Ser. No. 07/811,103, filed 20 Dec. 1991, now abandoned.

The present invention provides a new method of making organic compounds. In particular, the present invention provides a new reduction method for making certain pharmaceutically active compounds, such as thiazolidinedione derivatives, including pioglitazone, ciglitazone, englitazone and CS-045. These compounds are known for the treatment of diabetes and as insulin sensitizing agents.

BACKGROUND

Pioglitazone hydrochloride (($\pm$)-5-[4-[2-(5-ethyl-2-pyridyl)ethoxy]benzyl]-2,4-thiazolidinedione monohydrochloride), a thiazolidinedione derivative, is currently under clinical evaluation and is expected to effectively ameliorate the abnormal glucose and lipid metabolism associated with NIDDM or obesity (cf. Y. Momose et al., Chem. Pharm. Bull., 39:1440 (1991)).

T. Sohda, et al., J. Med. Chem. 35:2617-2626 (1992), discloses additional thiazolidinedione derivatives as potent hypoglycemic and hypolipidemic agents. including 5-[4-[2-(5-methyl-2-phenyl-4-oxazolyl)ethoxy]benzyl]-2,4-thiazolidinedione, which had the most potent activity, more than 100 times that of pioglitazone.

Another thiazolidine derivative under-going clinical studies as a hypoglycemic agent is englitazone sodium, 5-([3, 4-dihydro-2-(phenylmethyl)-2H- 1-benzopyran-6-yl[methyl]-2,4-thiazolidinedione sodium salt) (cf. D. A. Clark et al., J. Med. Chem., 34:319-325 (1991)).

Ciglitazone (($\pm$)-5- [4- [(1-methylcyclohexyl)methoxy] benzyl]-2,4-thiazolidinedione) is characteristic of a new class of thiazolidine antidiabetic agents which lower blood glucose in animal models of noninsulin diabetes mellitus (NIDDM), while actually reducing circulating concentrations of insulin. This is believed to be accomplished by improving the responsiveness of the peripheral tissues to insulin. See, e.g., Chang, et al, Diabetes 32:830–838 (September 1983).

CS-045 is an antidiabetic, thiazolidinedione derivative. Its activity and preparation are described in Drugs Fut. 1991, 16(9).

Also, thiazolidine derivatives useful for the treatment of diabetes are described in U.S. Pat. Nos. 4,287,200; 4,687, 777; and 4,572,9 12. Their effect on insulin resistance are described, e.g. in, Chang, et al, Diabetes 32:839–845 (1983) and Chang, et al. Diabetes 32:830–838 (1983).

The preparation of these thiazolidinedione derivatives, especially pioglitazone hydrochloride, includes the reduction of an intermediate previously performed by a troublesome high pressure hydrogenation on a palladium on carbon catalyst. What is needed in the art is an easier, more efficient method for perfoming this reduction.

INFORMATION DISCLOSURE

Y. Momose et at., Chem. Pharm. Bull., 39:1440 (1991); K. Meguro et al., Japan. Patent 139182 (1988); Chem. Abstr., 109:6504h (1988); disclose the process for making thiazolidinedione-derivatives, including pioglitazone, using hydrogen on a palladium on carbon catalyst.

D. A. Clark et at., J. Med. Chem., 34:319–325 (1991) discloses the process for making substituted dihydrobenzopyran and dihydrobenzofuran thiazolidine-2,4-diones, including englitazone, using hydrogen on a palladium on carbon catalyst.

Drugs Fut. 1991, 16(9) discloses the multistep process, via carbon alkylation, for the preparation of the thiazolidinedione CS-045.

The following references disclose cobalt catalyzed reductions: U. Leutenegger et al., Angew. Chem. Int. Ed., 28:60 (1989) discloses the enantioselective reduction of $\alpha,\beta$-unsaturated carboxylates with sodium borohydride and catalytic amounts of chiral cobalt semicorrin complexes; and M. N. Ricroch and A. Gaudemer, J. Organometal. Chem., 67:119 (1974) discloses (pyridinato) cobaloxime, chloro (pyridinato) cobaloxime and vitamin B$_{12}$ catalyzing the hydrogenation of $\alpha,\beta$-unsaturated esters by hydrogen or sodium borohydride.

J. O. Oshy, et al., J.A.C.S. 108:67–72 (1986), discloses cobalt (II)-mediated sodium borohydride and lithium aluminum hydride reductions, which do not involve the use of ligands.

SUMMARY OF THE INVENTION

The present invention particularly provides:

A process for preparing a compound of the formula I (refer to Formula Chart below)
wherein $X_1$ is an organic residue; which comprises:
(a) reacting a compound of the formula II with a cobalt ion, a ligand and a reducing agent;

This process wherein the temperature is -20° to 45° C. and wherein a suitable solvent is used;

This process wherein $X_1$ is the residue of an antidiabetic compound;

This process wherein $X_1$ is
(a) aryl, or
(b) Het;
wherein aryl is phenyl or naphthyl substituted by zero to three of the following:
(a) $C_1$-$C_3$ alkyl,
(b) hydroxy,
(c) $C_1$-$C_3$ alkoxy,
(d) halo,
(e) amino,
(f) mono- or di-$C_1$-$C_3$ alkylamino,
(g) nitro,
(h) mercapto,
(i) $C_1$-$C_3$ alkylthio,
(j) $C_1$-$C_3$ alkylsulfinyl,
(k) $C_1$-$C_3$ alkylsulfonyl,
(l) —NH—$C_1$-$C_3$ alkylsulfonyl,
(m) —N$C_1$-$C_3$ alkyl-$C_1$-$C_3$ alkylsulfonyl,
(n) SO$_3$H,
(o) SO$_2$NH$_2$,
(p) —CH$_2$NH$_2$,
(q) —A$_1$—(CH$_2$)$_n$-Het,
(r) —A$_1$—(CH$_2$)$_n$-($C_1$-$C_6$ alkyl substituted cyclohexyl), or
(s) —A$_1$—(CH$_2$)$_n$- cyclohexyl;
wherein A$_1$ is
(a) O, or
(b) S;
wherein Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a phenyl ring; which heterocycle ring is substituted by zero to three of the following:
(a) $C_1$–$C_6$ alkyl,
(b) hydroxy,
(c) hydroxy ($C_1$–$C_5$ alkyl),
(d) halogen,
(e) amino,
(f) amino ($C_1$–$C_5$ alkyl),
(g) nitro,
(h) mercapto,
(i) mercapto ($C_1$–$C_5$ alkyl),
(j) —$SO_3H$,
(k) —$SO_2NH_2$,
(l) —O—$C_1$–$C_5$ alkyl,
(m) —$(CH_2)_n$- aryl, or
(n) —$(CH_2)_n$- cyclohexyl;
wherein n is zero to five, inclusive;

This process wherein $X_l$ is the moiety of formula III (refer to Formula Chart below) wherein $R_1$ is hydrogen;

wherein $R_2$ is
(a) —O—$(CH_2)$-(5-ethyl-2-pyridyl),
(b) —O—$CH_2$-(1-methylcyclohexyl),
(c) the moiety of formula IV (refer to Formula Chart below); or wherein $R_1$ and $R_2$ taken together are the moiety of formula V (refer to Formula Chart below);

This process wherein $X_l$ is the moiety of formula VI (refer to Formula Chart below);

This process wherein the cobalt ion is in the form of
(a) cobaltous chloride,
(b) cobaltous diacetate, or
(c) cobaltic chloride;

wherein the ligand is
(a) dimethylglyoxime,
(b) 2,2'-bipyridyl, or
(c) 1,10-phenanthroline;

wherein the reducing agent is
(a) sodium borohydride,
(b) lithium borohydride,
(c) potassium borohydride,
(d) tetraalkylammonium borohydride, or
(e) zinc borohydride;

This process wherein the cobalt ion is in the form of cobaltous chloride, the ligand is dimethylglyoxime and the reducing agent is sodium borohydride;

This process wherein the solvent is
(a) methanol,
(b) ethanol,
(c) i-propanol,
(d) acetone,
(e) dimethylformamide, or
(f) tetrahydrofuran;
provided, however, that if (d), (e) or (f) is the solvent, (a), (b), (c) or water must also be present;

This process wherein the temperature is 5° to 20° C. and the solvent is water and tetrahydrofuran;

This process wherein $X_1$ is the moiety of formula VI (refer to Formula Chart below);

This process which further comprises:
(b) reacting the compound of the formula I (refer to Formula Chart below) with hydrochloric acid to obtain a compound of the formula VII (refer to Formula Chart below).

Previously, the preparation of thiazolidinedione derivatives included the reduction of an intermediate done as a troublesome high pressure hydrogenation on a palladium on carbon catalyst. Surprisingly and unexpectedly, the present invention provides a new, more efficient method for performing this reduction which uses a cobaltous chloride/bidentate ligand/sodium borohydride catalyst system and the variations thereof as described below. This new reduction method is faster and easier and results in improved yield of the desired product. It is also more convenient to scale into production equipment since no high pressure apparatus is required.

By "organic residue" is meant the residue of an organic compound that would be compatible with the reaction conditions of the process of the present invention. Preferably, such a residue will be one that does not react with the reactants of the process of the present invention so that only the double bond at the 5-position of the thiazolidinedione ring will be reduced. The reactants of the present invention include a cobalt ion, a ligand and a reducing agent. Such an organic residue would be readily determined by one of ordinary skill in the chemical arts.

By "residue of an antidiabetic compound" is meant the organic moiety that is attached to the 5-position of a thiazolidinedione derivative, which derivative has antidiabetic activity, such as those described in Y. Momose et al., Chem. Pharm. Bull., 39:1440 (1991); K. Meguro et al., Japan. Patent 139182 (1988); Chem. Abstr., 109:6504h (1988); D. A. Clark et al., J. Med. Chem., 34:319–325 (1991); U.S. Pat. Nos. 4,287,200; 4,687,777; and 4,572,912; Drugs Fut 1991, 16(9); and J. Med. Chem. 35:2617–2626 (1992). The description of the preparation of the intermediates of these compounds of formula II is expressly incorporated by reference herein. The process of the present invention is preferably applicable to the commercially important thiazolidinediones, pioglitazone hydrochloride (the compound of formula VII in the Formula Chart,) ciglitazone (the compound of formula X in the Formula Chart), englitazone (the compound of formula XX in the Formula Chart), CS-045 (the compound of formula XXX in the Formula Chart) and the recently disclosed thiazolidinedione of formula XL. All of the intermediates of formula II may readily be prepared by procedures analogous to those described above by one of ordinary skill in the art.

By "aryl" is meant phenyl or naphthyl substituted by zero to three of the following: $C_1$–$C_3$ alkyl, hydroxy, $C_1$–$C_3$ alkoxy, halo, amino, mono- or di-$C_1$–$C_3$ alkylamino, nitro, mercapto, $C_1$–$C_3$ alkylthio, $C_1$–$C_3$ alkylsulfinyl, $C_1$–$C_3$ alkylsulfonyl, —NH—$C_1$–$C_3$ alkylsulfonyl, —N$C_1$–$C_3$ alkyl-$C_1$–$C_3$ alkylsulfonyl, $SO_3H$, $SO_2NH_2$, —$CH_2NH_2$,— $A_1$-$(CH_2)_n$-Het, —$A_1$—$(CH_2)_n$—($C_1$–$C_6$ alkyl substituted cyclohexyl), or —$A_1$—$(CH_2)_n$- cyclohexyl; wherein $A_1$ is O, or S;

By "Het" is meant a 5- or 6-membered saturated or unsaturated ring containing from one to three heteroatoms selected from the group consisting of nitrogen, oxygen, and sulfur, and including any bicyclic group in which any of the above heterocyclic rings is fused to a phenyl ring; which heterocycle ring is substituted by zero to three of the following: $C_1$–$C_6$ alkyl, hydroxy, hydroxy ($C_1$–$C_5$ alkyl), halogen, amino, amino ($C_1$ –$C_5$ alkyl), nitro, mercapto, mercapto ($C_1$–$C_5$ alkyl), —$SO_3H$, —$SO_2NH_2$, —O—$C_1$–$C_5$ alkyl, —$(CH_2)_n$- aryl, or —$(CH_2)_n$-cyclohexyl; wherein n is zero to five, inclusive.

The reaction temperature range for the process of the present invention is -20° C. to +45° C. The preferred range is +5° to +20° C. +15° C. is most preferred.

Solvents that will work in the process of the present invention include methanol, ethanol, i-propanol, acetone, dimethylformamide (DME) and tetrahydrofuran (THF); with the proviso that if acetone, DMFF or THF are used then a proton source, such as an alcohol, like the ones mentioned above, or water must also be present. The amount of such proton source required would typically be ≧1eq., but would be readily apparent to one of ordinary skill in the art. Water and tetrahydrofuran are a preferred solvent combination.

Cobalt is the preferred metal ion ($Co^{+2}$ or $Co^{+3}$). Sources of cobalt include $CoCl_2$ (cobaltous chloride) and $Co(OAc)_2$ (cobaltous diacetate) or $CoCl_3$ (cobaltic chloride).

By "ligand" is meant a complexing agent for a metal ion. In addition to dimethylglyoxime, which is the preferred ligand, other ligands that may be used are 2, 2'-bipyridyl and 1,10-phenanthroline, which should be used in at least a 1:1 mole ratio with the cobalt ion. Most preferred is the ligand to cobalt ratio of 50:1.

Sodium borohydride ($NaBH_4$) is the preferred reducing agent, but other borohydrides, such as lithium borohydride, potassium borohydride, tetraalkylammonium borohydride or zinc borohydride may be used.

By "halo" is meant the halogens: fluorine, chlorine and bormine.

CHART A

Chart A illustrates the preparation of pioglitazone hydrochloride using the new reduction step of the present invention.

The compound of formula A-1 is prepared as described in Y. Momose et al., Chem. Pharm. Bull., 39:1440 (1991); K. Meguro et al., Japan. Patent 139182 (1988); and Chem. Abstr., 109:6504h (1988); which are expressly incorporated by reference herein.

The compound of formula A-1 is reduced to the compound of formula A-2 using a cobaltous chloride/bidentate ligand/sodium borohydride catalyst system. These reactants may be varied, as described above, by one of ordinary skill in the art.

The compound of formula A-2 is converted to the hydrochloride salt of formula A-3 by procedures readily known and available to one of ordinary skill in the art, including the use of concentrated hydrochloric acid.

Below are detailed examples illustrating this new reduction method. The procedures of Example 3 are most preferred.

DETAILED DESCRIPTION OF THE INVENTION

The present invention is seen more fully by the examples below.

EXAMPLE 1

Reduction Step in the Preparation of Pioglitazone Hydrochloride (Formula A-3) Refer to Chart A.

Part A

A slurry of 3.544 g of the compound of formula A-1 in 45 ml of water is cooled to 3° C. and 0.51 ml of 50% sodium hydroxide is added. The resulting solution is then treated with 22 mg of dimethylglyoxime, and then 1.0 g of powdered blue indicating silica gel (containing about 0.7 wt % $CoCl_2$), 432 mg of sodium borohydride and 5.0 ml of dimethylformamide (DMF) are added in that order. A thin black slurry results. The reaction mixture is stirred at about 17° C. for 25 hours at which time high pressure liquid chromatography (LC) indicates no remaining starting material. The silica gel is removed by filtration and the flask and solids are rinsed with a little water. The combined flitrate and rinse are treated with a solution of 1.90 ml acetic acid in 14ml of water in order to precipitate the product. After stirring for 2 hours at room temperature, the solids are collected by filtration, rinsed with three-14 ml portions of water and vacuum dried at 60° C. overnight to provide 3.20 g of crude product of formula A-2.

Part B

This product is slurried with 3.2 g of magnesol in 70 nil of ethyl acetate for 2 hours at 70° C. This slurry is transferred to a soxlet extraction thimble aid the solids are extracted with hot ethyl acetate (100 ml) for 5 days. The volume of the product slurry is adjusted to 70 ml by distillation and then the temperature is lowered to 50° C. and 2.2 ml of concentrated hydrochloric acid is added. The resulting slurry of the hydrochloric acid (HC 1) salt is stirred at 50° C. for 1 hour and then cooled to 0° C. The solids are collected, rinsed with three-8 ml portions of room temperature ethyl acetate and dried at 60° C. overnight to give 3.025 g of the title product.

EXAMPLE 2

Reduction Step in the Preparation of Pioglitazone Hydrochloride (Formula A-3) Refer to Chart A.

Part A

To a 100 ml 3-necked round bottomed flask, equipped with mechanical stirrer, is charged 1.772 g of the compound of formula A-1, 25 ml of water, 6.0 ml of tetrahydrofuran, and 2.0 ml of 1.0N sodium hydroxide. The mixture is stiffed at 25° C. for 10 min. and cooled to 15° C. To the cooled mixture is added 0.05–0.50 ml of catalyst solution, prepared by dissolving 0.232 g of dimethylglyoxime and 0.012 g of cobaltous chloride •6 $H_2O$ in 5.0 ml of dimethylformamide, and then a solution of 0.378 g of sodium borohydride and 0.5 ml of 1.0N sodium hydroxide diluted with 3.5 ml of water is added at a rate of 0.1 ml/min. The reaction is stirred at 15° C. for 3 hours and then 2.6 ml of acetone is added to quench any remaining sodium borohyfdide. After stirring for 0.5 hours, the solution is extracted with three 15 ml portions of ethyl acetate, and then it is acidified by the dropwise addition of 2.3 ml of glacial acetic acid diluted with 5.0 ml of water. Upon acidification, the product precipitates as white solids. The slurry is cooled to 0° C. and stirred for 0.5 hours prior to filtration. The collected product is washed with three 15 ml portions of water and dried at 45° C. under vacuum. The yield of crude product of formula A-2 is 1.583 g.

Part B

The crude product of formula A-2 is converted to the hydrochloride salt title product by the method described in Example 1, Part B.

EXAMPLE 3

Reduction Step in the Preparation of Piogliazone Hydrochloride (Formula A-3) Refer to Chart A.

Part A

A slurry of 5.0 g of the compound of formula A-1 in 15 ml of water, 9 ml of tetrahydrofuran and 9.5 ml of 1N sodium hydroxide is treated with a solution of 42 mg of cobalt (II) chloride •H₂O in 4 ml of 1:1 aqueous tetrahydrofuran. The temperature is adjusted to 15° C. and a solution of 667 mg of sodium borohydride in 15 ml of water containing 1.8 ml of 1N sodium hydroxide is added dropwise while maintaining the temperature at 15° C. to 18° C. The reaction mixture is quenched with 5.3 ml of acetone and then extracted with ethyl acetate as described in Example 2. The aqueous layer containing crude product of formula A-2 is acidified to pH 6.5 using 9 ml of 20% aqueous acetic acid. The resulting slurry is treated with 25 ml of ethyl acetate and is stirred at 70° C. for 2 hours. After cooling the slurry to 15° C., the solids are collected, washed first with water and then with methanol followed by drying at 65° C. The yield of the product of formula A-2 is 4.75 g.

Part B

A 5.00 g sample of the above solids is slurried at room temperature in 30 ml of methanol and then treated with 1.0 equivalent of conc. hydrochloric acid in 13 ml of methanol. The slurry is stiffed at 24° C. until all of the solids dissolved (2 hours). The solution is concentrated by vacuum distillation to 20 ml. The solvent changes over to ethyl acelate by displacement vacuum distillation. The desired hydrochloride salt precipitates during this solvent exchange. The slurry is cooled to 2° C. and the solids are collected by vacuum filtration, washed with cold ethyl acetate and dried in the vacuum oven at 60° C. The pioglitazone hydrochloride salt weighed 5.06 g and showed 97.7% quality by LC analysis.

FORMULA CHART

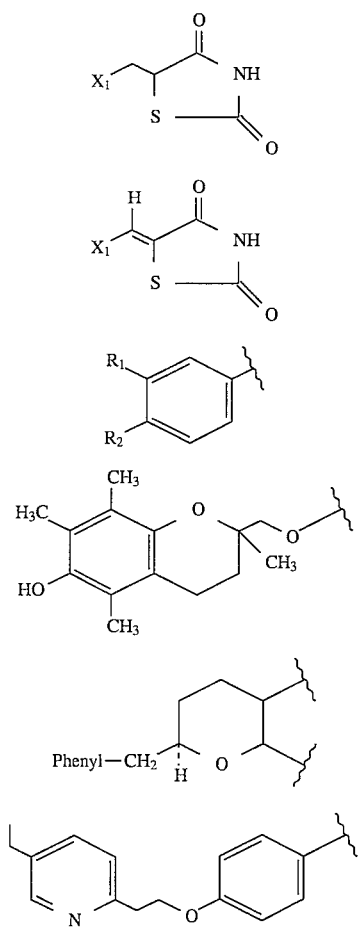

-continued
FORMULA CHART

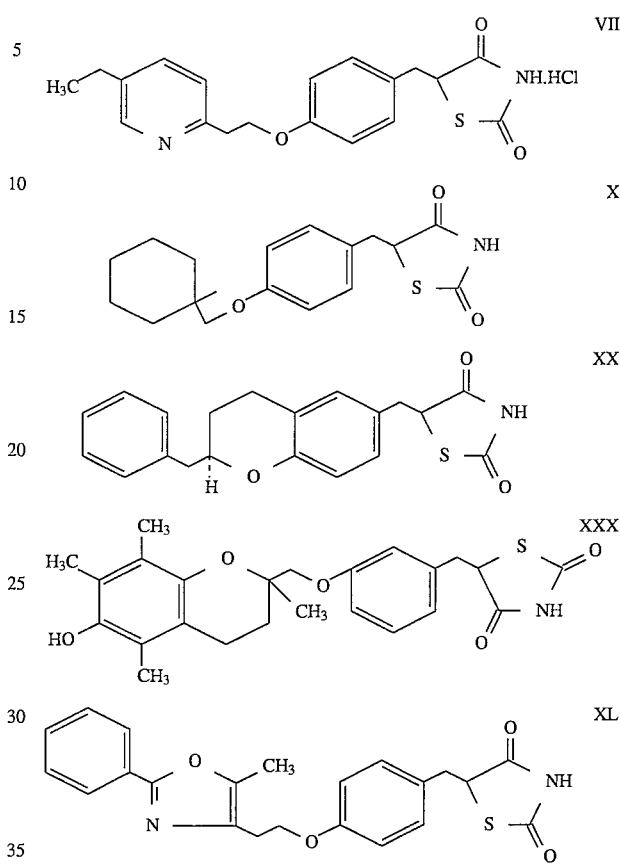

CHART A

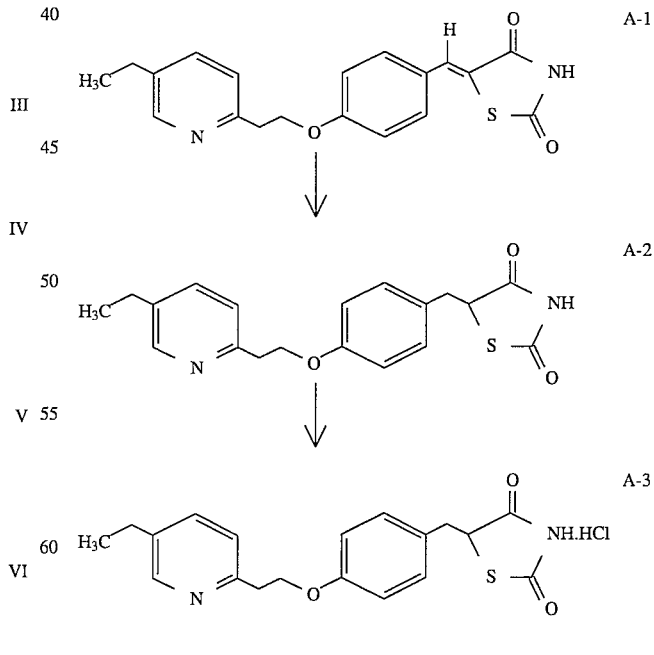

I claim:
1. A process for preparing a compound of the formula I wherein
X₁ is the moiety of formula III wherein
R₁ is hydrogen;
wherein
R₂ is
(a) —O—(CH₂)₂-(5-ethyl-2-pyridyl),
(b) —O—CH₂-(1-methylcylohexyl),
(c) the moiety of formula IV; or wherein
R₁ and R₂ taken together are the moiety of formula V which comprises:
(a) reacting a compound of the formula II with a cobalt ion, a ligand and a reducing agent in a suitable solvent. wherein the cobalt ion is in the form of
(a) cobaltous chloride,
(b) cobaltous diacetate, or
(c) cobaltic chloride;
wherein the ligand is
(a) dimethylglyoxime,
(b) 2,2'-bipyridyl, or
(c) 1,10-phenanthroline;
wherein the reducing agent is
(a) sodium borohydride,
lithium borohydride,
potassium borohydride,
(d) tetraalkylammonium borohydride, or
zinc borohydride.
2. The process of claim 1 wherein the temperature is −20° to 45° C.
3. The process of claim 2 wherein the temperature is 5° C. to 20° C.
4. The process of claim 1 wherein the cobalt ion is in the form of cobaltous chloride, the ligand is dimethylglyoxime and the reducing agent is sodium borohydride.
5. The process of claim 1
wherein the solvent is
(a) methanol,
(b) ethanol,
(c) i-propanol,
(d) acetone,
(e) dimethylformamide, or
(f) tetrahydrofuran;
provided, however, that if (d), (e) or (f) is the solvent, (a), (b), (c) or water must also be present.
6. The process of claim 5 wherein the solvent is water and tetrahydrofuran.
7. The process of claim 4 wherein X₁ is 8. The process of claim 7 which further comprises:
(b) reacting the compound of the formula I with hydrochloric acid to obtain a compound of the formula VII

* * * * *